United States Patent [19]

Hochgraf

[11] Patent Number: 5,274,243
[45] Date of Patent: Dec. 28, 1993

[54] CYLINDRICAL ALLUMINATION SYSTEM FOR INSPECTION OF SHEET MATERIAL

[75] Inventor: Neil A. Hochgraf, Rochester, N.Y.

[73] Assignee: Eastman Kodak Company, Rochester, N.Y.

[21] Appl. No.: 891,498

[22] Filed: May 29, 1992

[51] Int. Cl.⁵ .................. G01N 21/88; F21V 7/00
[52] U.S. Cl. ........................... 250/572; 356/430; 362/299; 362/96
[58] Field of Search ......... 250/572, 571, 216, 562–563; 356/429–431, 446, 445; 359/599; 362/297–299, 310, 96

[56] References Cited

U.S. PATENT DOCUMENTS

| | | | |
|---|---|---|---|
| 4,004,152 | 1/1977 | Ohser et al. | 250/572 |
| 4,038,554 | 7/1977 | Craig | 250/572 |
| 4,277,177 | 7/1981 | Larsen et al. | 356/431 |
| 4,311,393 | 1/1982 | Bartke | 356/448 |
| 4,532,430 | 7/1985 | Röss et al. | 250/572 |
| 4,801,810 | 1/1989 | Koso | 250/572 |
| 4,890,924 | 1/1990 | Beckstein | 356/429 |
| 4,914,308 | 4/1990 | Hochgraf | 250/572 |
| 5,066,865 | 11/1991 | Wennerberg | 356/446 |
| 5,087,822 | 2/1992 | Fairlie et al. | 356/446 |

Primary Examiner—Michael Messinger
Attorney, Agent, or Firm—Stephen C. Kaufman

[57] ABSTRACT

A tubular illuminator for focusing a bright line of approximately specular illumination onto the surface of a web moving at high speed to detect defects usually in the surface of the web. The illuminator in one embodiment comprises an elongated glass cylinder having reflective Fresnel ring facets or grooves on the major portion of the interior surface thereof extending the length of the glass tube, an elongated cylindrical lens assembly positioned inside the elongated tube adjacent and interior surface thereof devoid of the fresnel grooves, a mirror surfaced lens assembly housing for positioning the elongated lens assembly within the elongated cylinder in relation to an elongated slit diffuser extending axially through substantially the entire length of the glass cylinder, and an elongated line lamp disposed within the cylinder and extending in parallel to the diffuser-slit, so that light emitted by the elongated lamp is specularly reflected by mirror surfaces as reflective Fresnel facets and is directed or focused onto diffuser-slit and refocused by the lens assembly as bright line illumination or scanning an adjacent moving web surface.

19 Claims, 4 Drawing Sheets

CYLINDRICAL ALLUMINATION SYSTEM FOR INSPECTION OF SHEET MATERIAL

BACKGROUND OF THE INVENTION

1. Field of the Invention

This invention relates to cylindrical bright light sources for scanning and inspecting rapidly moving webs for surface defects therein.

2. Description of the Prior Art

Web inspection for the detection and classification of imperfections in the surface source through moving webs is an area of growing industrial interest. Such imperfections include stains and absorbing imperfections, abrasions and scattering imperfections, pinch marks, impurities preventing local processing, tears, through-holes, thickness imperfections, and other far side and near side imperfections that may print through to the surface of the thin (e.g. 0.002-0.020") webs usually being inspected. Such webs are typically inspected by a camera viewing through a lens subtending a small angle at its observing location. Such inspection conditions make it possible to detect differences in the light intensity detected by the camera due to scattering imperfections on or in the web as it is moved rapidly past the camera. Thus, line scan cameras or detectors are positioned with respect to the normal surface deflection angle to record the incidences of improper angular reflection in relation to the actual position of the web at the time. The actual position of defects may be recorded for slower speed examination or for other quality control purposes.

In my U.S. Pat. No. 4,914,308, one current system for scanning fast moving webs of paper, steel and aluminum sheet or transparent film substrates, employs high intensity, incandescent lamps having an elongated slit aperture or window with an elongated bar-shaped lens is employed to direct a strip of light across a fast moving web. The light is reflected or transmitted by the web toward a video camera or Charge Coupled Device (CCD) array which detects the intensity of the transmitted or reflected light for display on a monitor and for recording. Due to the high speed switching capabilities of full field video cameras and CCD linear arrays, is possible to derive closely-spaced lines of data while the web is moving at very high speeds. Each CCD detector site views a corresponding area along the transverse line of the moving web illuminated by bright light focused on it.

As described more completely in U.S. Pat. Nos. 4,914,308 and 4,752,897, both incorporated herein by reference in their entireties, the resulting stream of intensity modulated, digital data is input to a computer programmed to process the data to reveal and record defect related data. Through data compression techniques, the scanned lines may be displayed in slow motion on the video monitor. In data compression, normal transmitted or reflected light intensity signal values may be dropped out, highlighting signal values which correspond to a defect. Since defects are typically introduced by up-stream processing or transporting of the web, the defects are typically repetitive and appear as a vertical line on the display. Thus an operator is alerted to surface defects as they begin to appear and can make real time corrections while the web is moving or can shut down the web to inspect the equipment. At the same time, the defect data is stored in memory in relation to stored position values picked up as the web is moved through the scanning station so that the web may be visually inspected in those locations.

Such illuminators often have a length corresponding to the width of the web to be inspected. For example, illuminators used in paper and sheet metal fabrication are often seven feet long and eight inches square in cross-section and employ long incandescent or fluorescent lamps. Fluorescent lamps are not intrinsically bright, and it often becomes necessary to drive the lamps hard electrically, over their ratings, and place them fairly close to the web. Bright illumination is necessary because imperfections are often small, of low modulation, move past the inspection station rapidly and occasionally only detectible under special illuminating conditions. Such illuminators get quite hot, and the heat changes the glass pressure within the fluorescent lamp, affecting light output and tends to damage plastic optical components. Cooling of such illuminators is usually difficult in the restricted confines at the web inspection station and because of the small cross-section and long length of the illuminator.

Another method of inspection requires a polygon-shaped mirror or holographic scanning system to scan a laser beam across the web. Rotating mirror laser beam scanners require high precision, motor driven rotating mirror facets and optical systems for scanning the laser light beam accurately across the web with equal intensity of the beam reaching the extreme positions of scan in the relatively flat scanning angle. Aside from safety precautions inherent with the use of a high intensity laser beam and imperfections in the facets of polygon shaped mirrors, laser beams do not provide the white light source which is useful in identifying imperfections of differing color on or in the web being scanned.

Various cylindrical, linear light sources have been disclosed in the prior art for use in web inspection and also for use in telecine and the radiographic image scanning. In such scanners, it is common to provide an illumination system which produces a line of light across the film. The light source in such systems produces a circularly symmetric light beam, and a problem in these systems is to provide for an efficient conversion of the circular beam to a uniform line distribution of the light. U.S. Pat. No. 4,868,383 assigned to the assignee of the present application discloses a linear light source for a film scanner that includes an elongated cylindrical integrating cavity having diffusive reflective walls and an input port through which an intense beam of light is introduced into the cavity. An output slit parallel to the long axis of the cylindrical integrating cavity emits a line of light which may be transmitted by or reflected from moving film. Light transmitted by or reflected from the film is imaged onto a CCD linear array or a photo sensor.

Other linear light sources are employed in plain paper photocopying and other applications where the line of light produced by the integrating cavity is highly diffuse so that artifacts on the media being scanned, such as scratches, fingerprints or the like, will not appear in the image produced from the scanned information. Thus, in systems of that type it is highly desirable to avoid detecting surface defects and irregularities while providing sufficient light of constant intensity along the length of the line of light to be modulated by the varying densities of the images in degrees allowing differentiation of the image's gradation by the CCD or photo sensor.

Such a linear light source for a photocopier is illustrated in U.S. Pat. No. 3,947,106.

The environments in which these scanning systems are used are relatively clean. By contrast, industrial web inspection is often conducted under hot and dirty conditions with either dust or oil mist in the air which accumulates on the scanning equipment. Such accumulated dust or mist attenuates the light output and the heat accentuates the difficulty in cooling the high intensity light source.

It is preferable to employ a fixed, linear light source which provides an elongated light beam that is tailored to provide equal intensity light output alone its length and where the light is narrowly focused onto the web. Such constantly on light sources take advantage of the exposure accumulation properties of CCD elements.

SUMMARY OF THE INVENTION

It is therefore an object of the present invention to provide an efficient, uniform, line illuminator for the inspection of high speed moving webs of poorly reflecting or poorly transmitting media.

It is a further object of the present invention to provide for such web inspection for the detection and classification of imperfections employing a narrow line of approximately specular illumination.

It is a further object of the present invention to provide a compact, energy efficient and economical line illuminator for web inspection operating with a minimum amount of input energy, thereby minimizing cooling requirements and overall size of the illuminator.

It is a still further object of the present invention to provide a linear light source, which is positioned in a protective housing, for illuminating a web by directing light from a long, narrow window or aperture onto it, and a wiping mechanism for cleaning the exterior of the linear light source within the housing when necessary to remove obstructing, absorbing, scattering or redirecting deposits which may cause spurious imperfection responses in the inspection system.

These and other objects of the present invention are realized in the several embodiments thereof which employ a tubular illuminator for focusing a bright line of approximately specular illumination onto the surface of a web moving at high speed to detect imperfections in or on the web. The illuminator in one embodiment comprises an elongated glass cylinder having reflective Fresnel ring facets or grooves on the major portion of the interior surface thereof extending the length of the glass tube, an elongated cylindrical lens assembly positioned inside the elongated tube adjacent and interior surface thereof devoid of the Fresnel grooves, a mirror-surfaced lens assembly housing for positioning the elongated lens assembly within the elongated cylinder in relation to an elongated slit diffuser extending axially through substantially the entire length of the glass cylinder, and an elongated line lamp disposed within the cylinder and extending in parallel to the slit-diffuser, so that light emitted by the elongated lamp is specularly reflected by the reflective Fresnel facets and is collected by the slit-diffuser and focused by the lens assembly as bright line illumination for scanning an adjacent moving web surface.

The elongated cylinder is preferably enclosed within an elongated, cylindrical, opaque housing having an elongated aperture therein adjacent to the lens assembly for allowing the bright line of illumination to pass therethrough, wherein the opaque cylinder is in addition coupled to a source of cleaning fluid for directing cleaning fluid over the glass cylinder passed the exit window and collected through a drain in the protective cylinder. The protective cylinder is further provided with a wiper mechanism for wiping the exterior surface of the glass cylinder and removing the cleaning fluid in the process.

In a further embodiment, the glass cylinder may be illuminated with light directed through one or both of the transparent ends thereof and through optical filters and/or diffusers for tailoring the spectral characteristics of the bright line of illumination to the characteristics of the scanning web to satisfy the accuracy and other requirements of the inspection analysis while achieving artifact free uniformity.

BRIEF DESCRIPTION OF THE DRAWINGS

These and other objects, advantages and features of the present invention will become apparent upon reference to the following description of the preferred embodiments thereof when read in light of the attached drawings wherein like elements are referenced by like numerals, and wherein.

DESCRIPTION OF THE PREFERRED EMBODIMENTS

Figure 1:
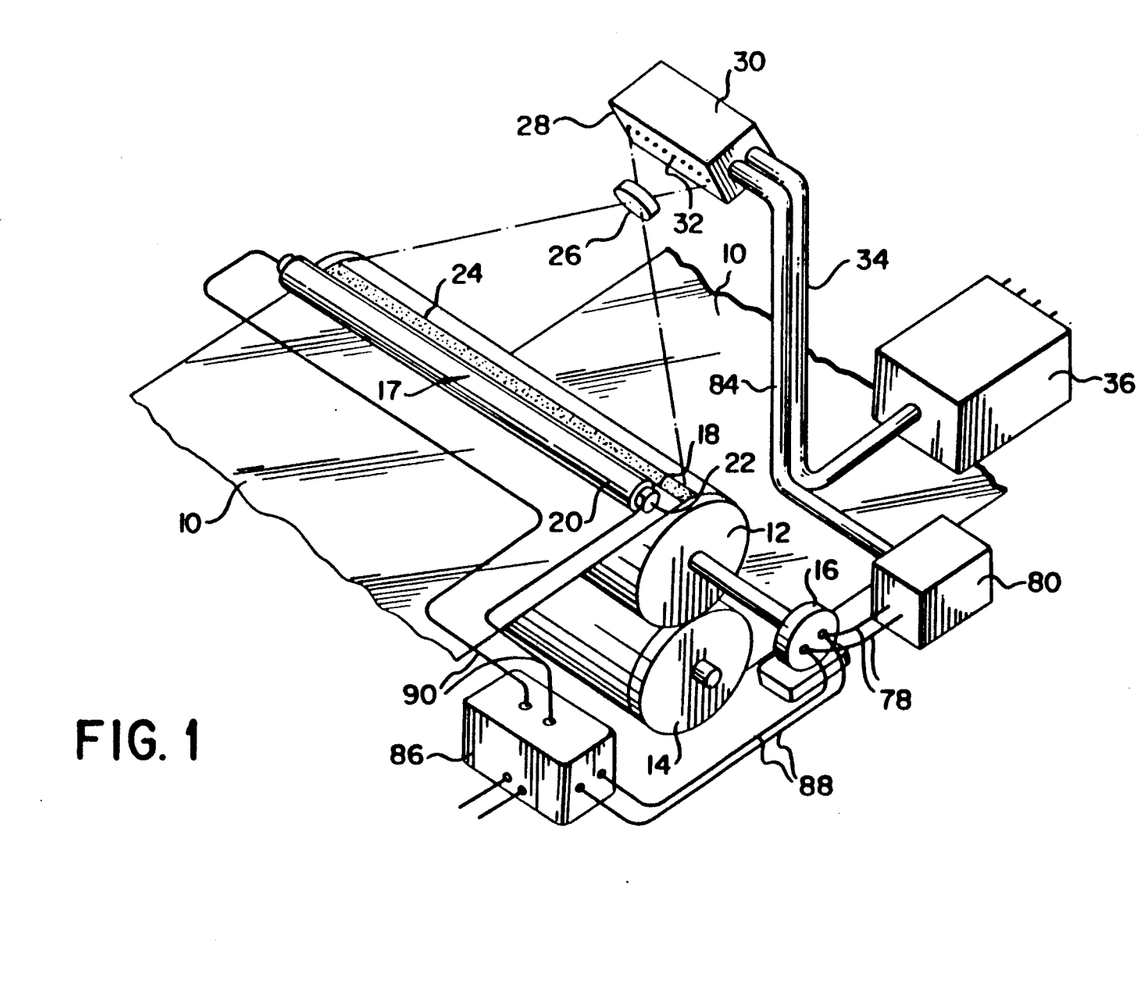
FIG. 1 is a schematic perspective view of moving web scanning apparatus.

Turning now to FIG. 1, it illustrates in a simplified perspective view of a web inspection station of the type disclosed in my above-incorporated '308 patent in which the linear light source 17 of the present invention may be implemented for inspecting the surface of a web 10 advanced thereby. The web 10 is shown being moved longitudinally while being wrapped around rollers 12 and 14. A line of light is emitted from a slit extending lengthwise of linear light source 17 and directed onto the surface of the web 10 in a bright line 24. The light 24 striking the surface of web 10 is reflected toward a lens 26 onto detector face 28 of a conventional linear CCD array or camera 30 which produces an electrical output signal as the CCD elements are scanned electronically in a manner known in the art. The output signal is fed by cable 34 to signal processing circuitry in box 36 and thereafter to a recording and display system (not shown). Other elements illustrated in FIG. 1 are employed in accordance with the teachings of the '308 patent and are not important to the present invention.

Such web inspection systems as depicted in FIG. 1 may process the detected signals to largely disregard or drop out signals which fall within a normal amplitude indicative of an acceptable surface and retain in memory for display those signals which, by their amplitude, position or other characteristic are imperfections of the particular web being scanned. The reflected signals may be enhanced to emphasize the imperfections depicted on the visual display. Such web scanning systems are employed to illuminate webs many feet wide and moving at high speed. More than one CCD array and lens system or video camera may be employed in a side-by-side arrangement in order to inspect linear sections of the width of a wide web 10.

Usually, the imperfections which are imparted in a web during processing extend longitudinally and occasionally laterally in the web in a continuous or repetitive pattern. Consequently, the operator is alerted to a defect rather quickly as the individual scanning lines displayed in the video monitor present a recognizable pattern. In addition such patterns may be recognized as defects by monitoring software or electronic inspection apparatus in box 36.

As illustrated in FIG. 1, linear light sources 17 for web scanners are typically located quite close to the web 10 which is usually being fabricated or milled upstream of the inspection station and moving past at a rapid speed, e.g. 1000 feet per minute. The focal length of the lens 26 is typically between 20 mm and 50 mm, and the angles of incidence and reflection in the line 24 are typically between 10 and 20 degrees of normal. The continuous air movements generated by the fast moving web 10 splatter or deposit a film of particles, dust, or oil mist on the exterior surface of the linear light source 17 which is usually hermetically sealed to prevent the contamination of the elongated lamp contained inside and the interior optical surfaces. The hermetic sealing thus usually overlays the exit aperture and typically constitutes a layer of transparent glass or an elongated lens system of the types depicted in the above incorporated '308 patent.

Figure 2:
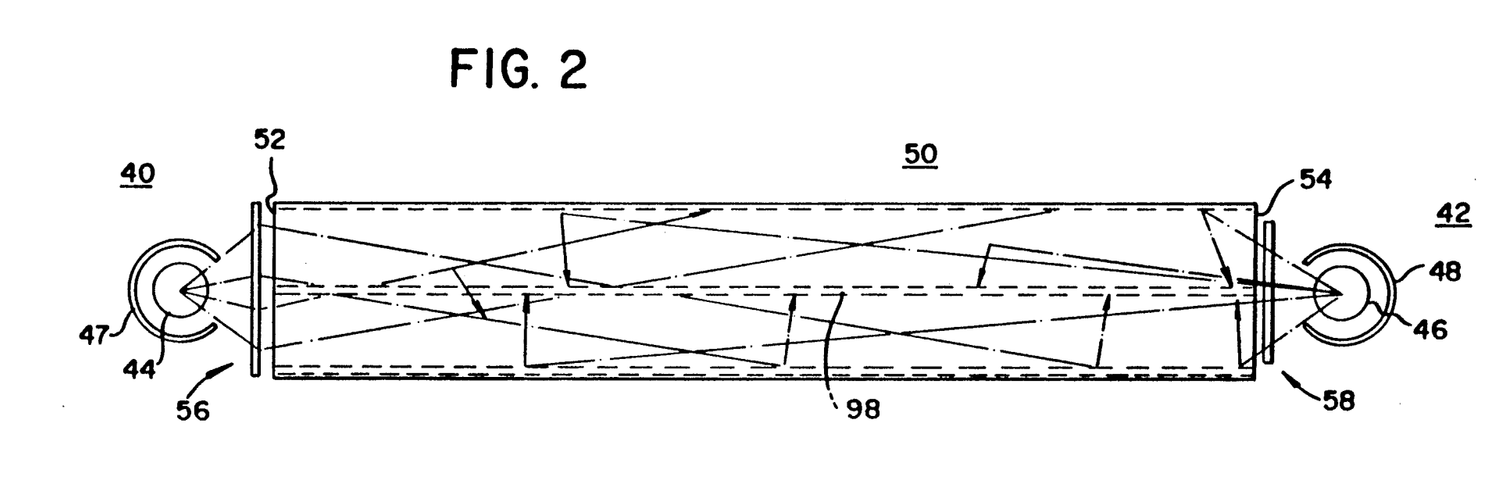
FIG. 2 is a side view of an elongated, linear light source of one embodiment of the present invention employing end light pumping and Fresnel facets to scatter the light and distribue it evenly to the elongated lens system.

Turning now to FIG. 2, it illustrates a side view of one preferred embodiment of the linear light source of the present invention. In FIG. 2, a pair of light sources 40 and 42 direct light into the ends 52 and 54 of an elongated glass tube 50 which is constructed in a manner to be described to emit light in a line onto the web 10. The interior surface of the tube 50 is provided with reflective Fresnel ring facets 60 extending circumferentially around the inner diameter except where a cylindrical lens is positioned as shown in the cross-section views of FIGS. 4 and 5.

Figure 3:
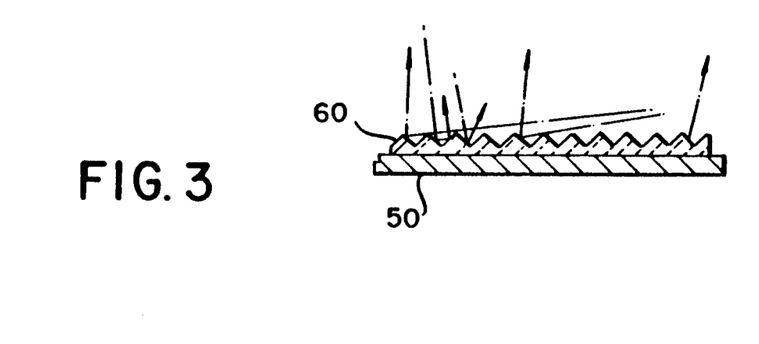
FIG. 3 is a partial, enlarged section of reflective Fresnel grooved interior surface of the linear light source of FIG. 2.

The light sources 40 and 42 each comprise lamps 44 and 46 housed in reflectors 47 and 48, respectively. Optical filters 56 and 58 may be provided to filter out undesired wavelengths emitted by the lamps 44 and 46. The light beams passing through the filters 56 and 58 strike the internal Fresnel rings 60 illustrated in FIG. 3. The light rays traveling axially strike and are reflected by the Fresnel rings 60 and distribute the light throughout the length of the glass tube 50 before the light is emitted through the cylindrical lens. The circular cross-section glass tube 50 provides a light collecting, focusing and relay lens enclosing cavity 51. The cylindrical nature of the reflector also help to smooth out the image of lamp supports.

Figure 4:
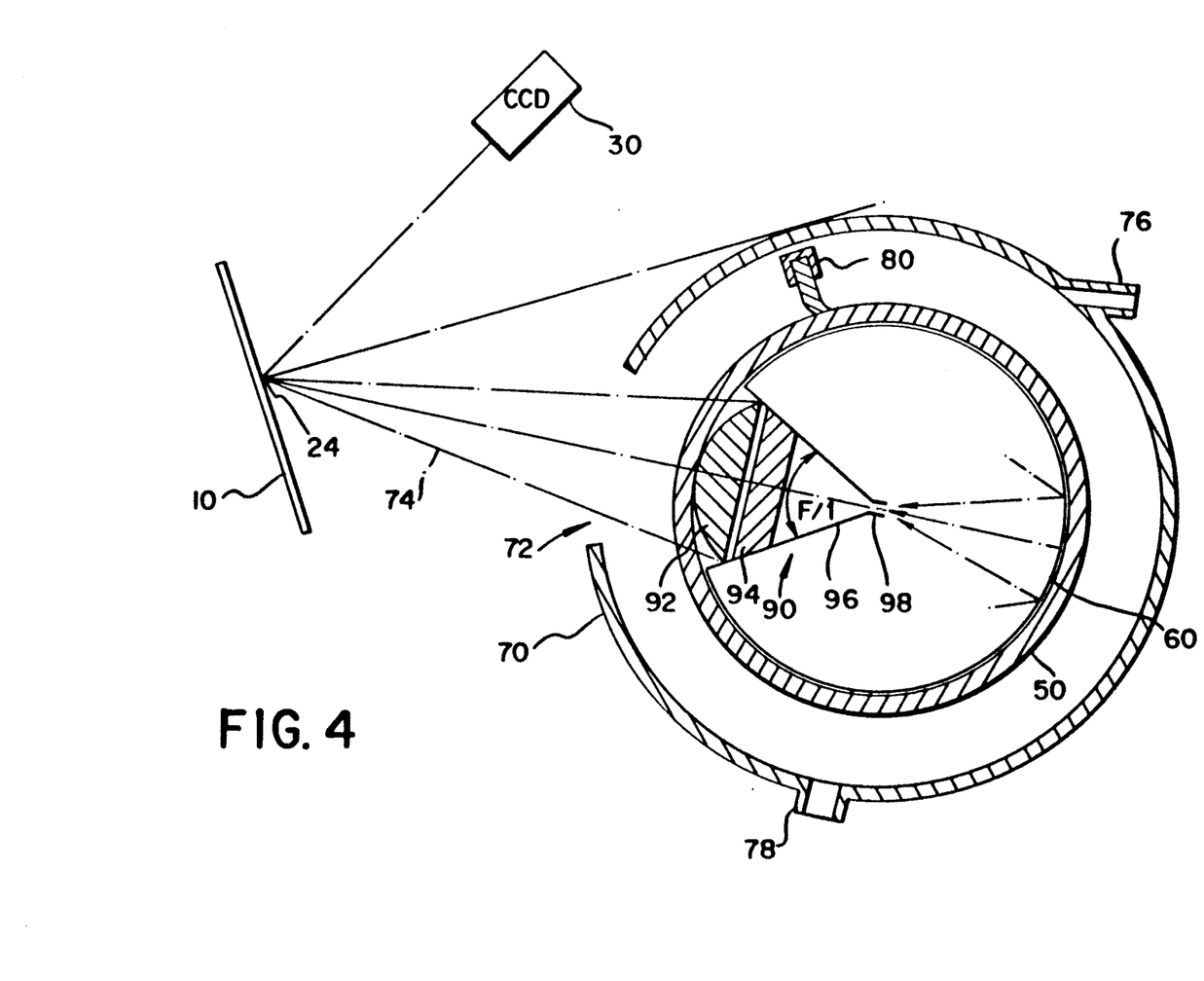
FIG. 4 is an end view in partial cross-section of a linear light source of a type shown in FIG. 2 and a circumferentially moving wiper assembly positioned inside a protective housing in accordance with a further embodiment of the invention.

Turning now to FIG. 4, it illustrates a partial cross-section view of a first embodiment of the linear light source which includes the glass tube 50 of FIG. 2 positioned in a protective cylindrical housing 70 and having an elongated wiper blade 80 located in the space between the outside surface 53 of the tube 50 and the protective cylindrical housing 70. An elongated relay lens system 90 is positioned in a pie-shaped, elongated enclosure 96 which extends the length of the integrating cavity 51 and is aligned with an elongated aperture 72 in the protective housing 70 to focus a bright line of light in the optical path 74 onto the moving web 10 which is tilted at an angle so that incident light is reflected toward a CCD linear array 30 as described in FIG. 1.

The lens system 90 acts as an optical relay consisting of first and second elongated cylindrical lens elements 92 and 94 fitted inside the side walls 96 which meet at the axis of the integrating cavity 50. A slit diffuser 98 is positioned at the focus of the Fresnel facets to collect light from the light sources 40 and 42 reflected off the Fresnel facets 60 and direct that light to the first and second lens elements 92 and 94. The weak diffuser 98 could be at or in the narrow slit which is on the order involved 0.05 inches wide. In that embodiment, in order to ensure that only the narrow width of the diffuser slit is focused onto the surface of the web 10, the interior surfaces of the side walls 96 are coated with a light absorbing black paint, the diffuser function being chosen to waste the least amount of light on the black painted surfaces. The exterior surfaces of the side walls 96 are mirror coated to increase reflectance of light within the focusing-collecting cavity 51.

The optical slit which acts as the entrance to the optical relay may be so simple as to be the unobstructed gap between the opposing side walls 90 of the elongated housing containing the optical relay lens elements. The function of the internal slit is to prevent illumination off the desired inspection line on the web, which is a particular problem with light sensitized product such as unexposed photographic film. The slit sharply defines the width of the line of illumination.

In this regard, the width of imaging pixels in a CCD camera can be a narrow as 0.0005", and even with a magnification of sixty times by the inspection camera lens, its position conjugates. This results in an inspection line of illumination that can be as small as 0.030" high and at worst may 0.1"–0.3" high. There is little point to intentionally illuminating a stripe of the web more than ten times the inspection line height, for that just wastes light and increases or duplicates response to imperfections. Such additional light also tends to reflect off adjacent structures and cause scattering onto the line-of-inspection which in turn tends to illuminate imperfections from large angles of incidence reduce the contrast of such imperfections.

Video cameras and CCD linear array elements are capable of discerning far greater light intensity variations from imaging pixel to pixel than the human eye. Although the slit is capable of directing light toward the optical relay and the cavity acts to distribute light from the lamps, it cannot eliminate all variations in the intensity of the light entering it along its length that may arise from the angles at which light is reflected from Fresnel facets, course high contrast structure and other spatial intensity variations, into the emitted line of illumination which an accurate camera can detect. Such intensity variations detected by the camera may in turn cause the monitoring software to misclassify the variations as imperfections in the web. These unnecessary background artifacts can be suppressed by putting a weak, almost transparent, diffusing material, e.g. a milky white scattering plastic or a denser opalescent glass bead into or immediately adjacent to the slit 98 which may act as a simple light pipe. It is sufficient that the diffuser material efficiently convey, but scramble the image content between the collected focused light and the following optical relay. The density or thickness of the diffuser material should be chosen to hide upstream defects, e.g. facet defects, glints, shadowed facet bottoms, and yet deliver most to the collected and focused illumination to the aperture of the optical relay for imaging onto the web in the cross illumination direction.

The illustrated lens element 94 could have optical power at right angles to the lens element 92. Lens element 92 re-images the diffuser element or slit 98 onto the surface of the web 10 being inspected. A further cylindrical lens 94 would help to make the line illuminator appear even more uniform to the observing camera or CCD linear array 18 by tending to make the ends of the line of light near or at the edges of the web 10 appear brighter.

Figure 5:
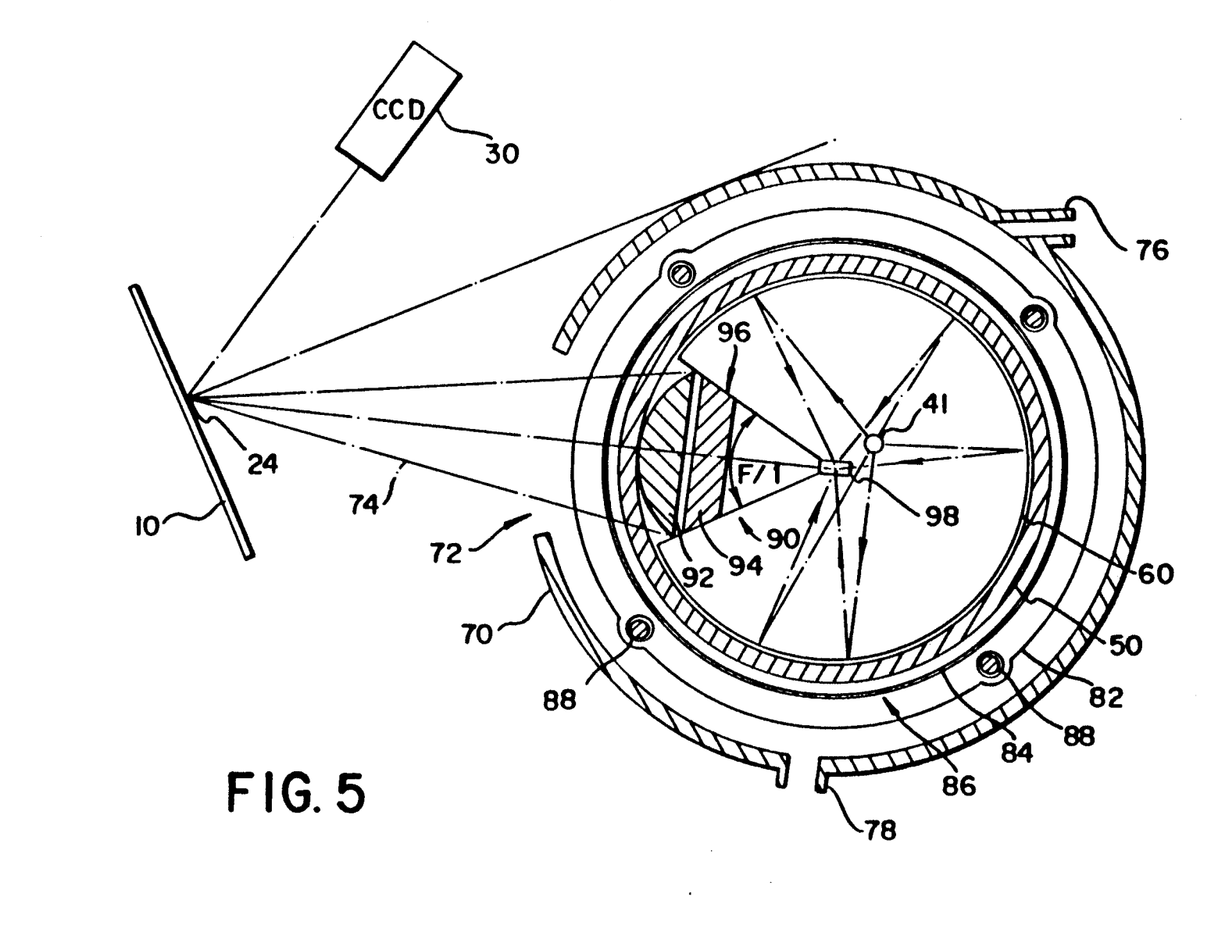
FIG. 5 is a further end view in partial cross-section of a further embodiment of a linear light source with an axially moving wiper mechanism positioned inside a protective housing. The drawings are not necessarily to scale.

Turning now to FIG. 5, it illustrates in partial cross-sections a combined assembly of the type described above in reference to FIG. 4 with modifications in the light source. FIG. 5 illustrates the use of an elongated, tubular lamp 41 extending lengthwise through the interior of the cavity 50 at a position slightly displaced from the axis of the cavity 50. The elongated light source 41 may constitute a tubular lamp or light pipe that emits light in 360° along its length toward the Fresnel facets 60 and the mirrored side walls 96 so that the emitted light is reflected back until it strikes the diffuser slit and element 98 and enters the interior of the pie shaped lens system 90. Such a lamp 41 may constitute a fluorescent, incandescent or halogen light source which by its nature may exhibit variable light output along its length. The lamp 41 supports spaced along the length of the tube 50 may also cast shadows and obstruct light output. The Fresnel ring facets 60 extending through about 300° around the circumference of the tube 50 act to reflect and distribute light emitted by lamp 41 in the manner described above to fill in such shadows and obstructions and the slit 98 preferably includes a diffuser element of the type described above to decrease variations caused thereby in the emitted line of illumination.

Turning now to the apparatus and method of cleaning the exterior glass surface of the light integrating cavity 50 at least in the region of the pie shaped lens assembly 90, the wiper blade 80 in the embodiment shown in FIG. 4 is provided for movement in the counter clockwise direction and back again while a cleaning fluid is injected into port 74 which may constitute a series of spaced openings along the length of the cylindrical protective housing 70. The cleaning fluid sprays against the exterior surface of the light collecting and focusing cavity 50 and the wiper 80 may be moved around the circumference of the cavity 50 to wipe off the cleaning fluid and direct it to the drain port or ports 78. In this fashion, dust and oil mist entering the slit 72 and deposited on the surface of the light integrating cavity 50 may be periodically removed without allowing it to fall on the moving web or other equipment. Pressurized air or gas may also be fed into these ports to prevent mist or dust from getting to the window. It will be understood that more than one wiper blade 80 may be provided and that movement may be effected manually or by motors mounted at the ends of the protective housing 70.

Turning now to the alternate cleaning arrangement, FIG. 5 illustrates the use of a ring-shaped wiper 82 which surrounds and contacts the exterior glass surface of the light integrating cavity 50. The circumferential wiper 82 comprises a wiper blade 84 and a retainer ring 86 which has four spaced apart holes 88 through which four rods or cables 89 extend lengthwise from one end of the protective housing 70 to the other. In use, the ring or partial ring wiper 82 is drawn back and forth by the drive method 89 so that the wiper 84 cleans the glass or plastic surface. As in the embodiment of FIG. 4, fluid is sprayed into the cavity through inlet port or ports 76 and drained away through drains 78 while the wiper blade 84 is drawn back and forth across the surface. When the cleaning assembly is not used, the narrow circumferential wiper 82 is positioned at one end or the other protective shield 70 away from the ends of the elongated window aperture 72.

The protective housing and cleaning assembly and method of its use may be utilized in conjunction with other linear light sources than the inventive light sources described above. The cleaning assembly alleviates the loss in light intensity minimizes the introduction of out-of-focus spurious defects and the length-wise irregularities in intensity caused by the build up of dust or oil along the length of the light emitting slit or stripe of the light collecting and focusing cavity. The protective housing 70 protects the fragile, glass, light integrating cavity 50 from damage by a loose or flopping web or mishandling.

With respect to the illustrated preferred embodiments of the linear light source, it will be appreciated that the assembly may be constructed in a relatively small diameter of about 6-10 inches by any desired length. The Fresnel facets in the arrangement of the lens assembly and the diffuser slit or element insure that light emitted by the end-mounted light sources 40, 42 or the linear element 41 is efficiently distributed down the length of the light integrating cavity which may extend for several feet and is artifact free. The efficient, uniform distribution of light contributes to the usefulness of the bright line of light of uniform intensity imaged onto the web 10.

Other modifications may be made to the light collecting cavity to enhance the distribution of light down its length. Although the illustrated embodiments depict an interior surface with uniform Fresnel grooves applied circumferentially through its entire length, it will be understood that the angulation, size and distribution of cylindrical Fresnel elements may be varied lengthwise to alter the light reflectance distribution. For example, the Fresnel ring-shaped elements may be tilted toward the ends 52 and 54 to a greater degree near the ends than the middle of the light integrating cavity 50. Alternatively, the lens elements may be enlarged to narrow the inner diameter of the light integrating cavity 50 at selected points along its length.

These and other modifications will be apparent to those skilled in the art. The invention has been described in detail with particular reference to preferred embodiments thereof, but it will be understood that variations and modifications can be effected within the spirit and scope of the invention.

What is claimed is:

1. An illumination system for inspection of sheet material for the identification of surface defects, said system being adapted to provide a line of illumination on the sheet material which is supported for movement past the line of illumination, said system comprising:

a light source for providing a light beam along an optical path in said system; and a light collecting, focusing and distributing cylinder located along said optical path for receiving light from said source and for producing a line of illumination on the surface of the sheet material, wherein the cylinder further comprises:

an elongated light integrating cavity having an interior surface and an interior surface treatment for enhancing the reflecting, distributing and focusing of light incident thereon;

an elongated lens assembly mounted interiorly within the light cavity for collecting and directing the line of illumination onto the sheet material; and diffuser means extending lengthwise in relation to the lens assembly for admitting light reflected from the interior surface of the light cavity and directing that light to the lens assembly.

2. The illumination system of claim 1 wherein said interior surface treatment of said light integrating cavity comprises Fresnel elements extending circumferentially around the interior surface of the light integrating cavity and extending through all or part of the length of the interior surface of the elongated light integrating cavity.

3. The illumination system of claim 1 wherein the elongated lens assembly is mounted within the cavity in a lengthwise extending housing and the diffuser means is an entrance means through which light reflected from the interior surface of the light integrating cavity is received, and then directed as a line of illumination onto the surface of the sheet material, the housing having reflective surfaces facing toward the interior of the light cavity for contributing to the distribution of light therein and absorbing surfaces interiorly for inhibiting reflectance of light entering the entrance means.

4. The illumination system of claim 1 wherein the light source comprises a linear light emitting lamp extending lengthwise interiorly of the light cavity and spaced from the diffuser means of the lens assembly so that light emitted thereby does not directly pass through the diffuser means, yet is focused upon the diffuser means by the interior surface treatment so spatial defects in the lamps emission are suppressed, yet efficiently transfer of light is effected.

5. The illumination system of claim 1 wherein said light source further comprises at least one lamp disposed at one end of the light cavity for directing a light beam against the interior surface of the light cavity.

6. The illumination system of claim 1 further comprising:

enclosure means for surrounding and protecting said cylinder having an elongated slit through which the line of illumination provided by the cylinder is directed, protecting the cylinder from damage;

wherein the cylinder has an external surface facing the enclosure means, wherein the enclosure means has an internal surface facing the cylinder, and wherein the internal surface of the enclosure means and the external surface of the cylinder form a space therebetween;

wiper means disposing within said enclosure means for wiping the external surface of the cylinder at least in the region of the slit in the enclosure means; and means for introducing a cleaning fluid or mist into the space between the enclosure means and the external surface of the cylinder and for collecting the cleaning fluid removed in cleaning off the external surface of the cylinder.

7. The illumination system of claim 6 wherein said wiper means comprises a ring-shaped wiper blade circling and in contact with the external surface of the cylinder; and means for drawing the ring wiper back and forth from one end to the other end of the cylinder to wipe the external surface thereof.

8. The illumination system of claim 6 wherein said wiper means further comprises:

at least one elongated wiper blade extending lengthwise of and in contact with the external surface of the cylinder; and means for drawing the wiper blade circumferentially around at least a portion of the external surface of the cylinder to wipe away dirt and cleaning fluid introduced in a cleaning operation.

9. An illumination system for inspection of sheet material for the identification of surface defect, said system being adapted to provide a line of illumination on the sheet material which is supported for movement past the line of illumination, said system comprising:

a light source for providing a light beam in an optical path in said system;

an integrating cylinder located along said optical path for receiving light from said source and for producing a line of illumination on the surface of the sheet material;

enclosure means for surrounding and protecting said integrating cylinder having an elongated slit through which the line of illumination provided by the integrating cylinder is directed for protecting the integrating cylinder from damage;

wherein the integrating cylinder has an external facing the enclosure means, wherein the enclosure means has an internal surface facing the integrating cylinder, and wherein internal surface of the enclosure means and the external surface of the integrating cylinder form a space therebetween;

means disposed within said enclosure means for cleaning the external surface of the integrating cylinder in at least in the region of the slit in the enclosure means; and means for introducing a cleaning fluid into the space between the enclosure means and the external surface of the integrating cylinder and for collecting the cleaning fluid removed in cleaning off the external surface of the cylinder.

10. The illumination system of claim 9 wherein said cleaning means comprises:

a ring-shaped wiper blade encircling and in contact with the external surface of the integrating cylinder; and means for drawing the wiper blade back and forth from one end to the other end of the cylinder to wipe its external surface.

11. The illumination system of claim 9 wherein said cleaning means further comprises:

at least one elongated wiper blade extending lengthwise of and in contact with the external surface of the integrating cylinder; and means for drawing the wiper blade circumferentially around at least a portion of the external surface of the integrating cylinder to wipe away cleaning fluid introduced in a cleaning operation.

12. An illumination system for inspection of sheet material for the identification of surface defects, said system being adapted to provide a line of illumination on the sheet material which is supported for movement past the line of illumination, said system comprising:
 a light source for providing a light beam along an optical path in said system; and
 an integrating cylinder located along said optical path for receiving light from said source and for producing a line of illumination on the surface of the sheet material, wherein the integrating cylinder further comprises:
  an elongated light integrating cavity having an interior surface and an interior surface treatment for enhancing reflection of light incident thereon;
  an elongated lens assembly mounted interiorly within the light integrating cavity for collecting and directing the line of illumination onto the sheet material; and
  diffuser means extending lengthwise in relation to the lens assembly for admitting light reflected from the interior surface of the light integrating cavity and directing it to the lens assembly.

13. The illumination system of claim 12 wherein said interior surface treatment of said light integrating cavity comprises Fresnel elements extending circumferentially around the interior surface of the light integrating cavity and extending through all or part of the length of the interior surface of the elongated light integrating cavity.

14. The illumination system of claim 12 wherein said elongated lens assembly mounted within the light integrating cavity extends lengthwise in a housing, wherein the diffuser means is an entrance means through which light reflected from the interior surface of the light integrating cavity is received and directed in a line of illumination on to the surface of the sheet material, the housing having reflective surfaces facing interiorly of the light integrating cavity for contributing to the distribution of light therein and absorbing surfaces interiorly for inhibiting reflectance of light entering the entrance means.

15. The illumination system of claim 12 wherein the light source comprises a linear light emitting lamp extending lengthwise interiorly of the light integrating cavity and spaced from the diffuser means which is an entrance means of the lens assembly so that light emitted by the lamp does not directly pass through the entrance means.

16. The illumination system of claim 12 wherein said light source further comprises at least one lamp disposed at one end of the elongated light integrating cavity for directing a light beam against the interior surface of the light integrating cavity.

17. The illumination system of claim 12 further comprising:
 enclosure means for surrounding and protecting said integrating cylinder having an elongated slit through which the line of illumination provided by the integrating cylinder is directed for protecting the integrating cylinder from damage;
 wherein the integrating cylinder has an external surface facing the enclosure means, the enclosure means has an internal surface facing the integrating cylinder, and the internal surface of the enclosure means and the external surface of the integrating cylinder form a space therebetween;
 means disposed within said enclosure means for cleaning the external surface of the integrating cylinder at least in the region of the slit in the enclosure means; and
 means for introducing a cleaning fluid into the space between the enclosure means and the external surface of the integrating cylinder and for collecting the cleaning fluid removed from cleaning off the external surface of the cylinder.

18. The illumination system of claim 17 wherein said cleaning means comprises:
 a ring-shaped wiper blade and circling and in contact with the external surface of the integrating cylinder; and
 means for drawing the cylindrical wiper back and forth from one end to the other end of the integrating cylinder to wipe the external surface thereof.

19. The illumination system of claim 17 wherein said cleaning means further comprises:
 at least one elongated wiper blade extending lengthwise of and in contact with the external surface of the integrating cylinder; and
 means for drawing the wiper blade circumferentially around at least a portion of the external surface of the integrating cylinder to wipe away cleaning fluid introduced in a cleaning operation.

* * * * *